United States Patent
Ito et al.

(10) Patent No.: US 9,615,729 B2
(45) Date of Patent: Apr. 11, 2017

(54) ENDOSCOPE DETECTING SYSTEM

(71) Applicant: OLYMPUS CORPORATION, Tokyo (JP)

(72) Inventors: Takeshi Ito, Hino (JP); Masahiro Nishio, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 61 days.

(21) Appl. No.: 13/936,283

(22) Filed: Jul. 8, 2013

(65) Prior Publication Data
US 2013/0296651 A1  Nov. 7, 2013

Related U.S. Application Data

(63) Continuation of application No. PCT/JP2012/050829, filed on Jan. 17, 2012.

(30) Foreign Application Priority Data

Jan. 24, 2011 (JP) .................................. 2011-011871

(51) Int. Cl.
A61B 1/04 (2006.01)
A61B 1/06 (2006.01)
(Continued)

(52) U.S. Cl.
CPC ............ *A61B 1/06* (2013.01); *A61B 1/00036* (2013.01); *A61B 1/0684* (2013.01); *A61B 1/00* (2013.01);
(Continued)

(58) Field of Classification Search
CPC ....... A61B 5/0084; A61B 5/0086; A61B 5/09; A61B 1/00036; A61B 2034/252; A61B 34/20; A61B 34/25

USPC ...... 600/117, 424, 473, 407, 114; 606/3, 33; 250/370.08

See application file for complete search history.

(56) References Cited

U.S. PATENT DOCUMENTS 4,396,945 A * 8/1983 DiMatteo et al. ............ 348/139
4,898,175 A * 2/1990 Noguchi ....................... 600/476
(Continued)

FOREIGN PATENT DOCUMENTS

JP   2002-028125 A   1/2002
JP   2009-142440 A   7/2009
(Continued)

OTHER PUBLICATIONS

International Search Report dated Mar. 6, 2012 issued in PCT/JP2012/050829.

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

An endoscope system includes an illumination unit which includes a modulation section configured to control a visible light source so that visible light from the visible light source is subjected to intensity modulation in a predetermined pattern, and emits modulated visible light as illumination light, a detection section configured to detect the modulated visible light, and a determination section configured to determine whether an insertion portion of an endoscope is present in an object based on a detection result of the detection section. The illumination unit is arranged outside the object, and the detection section is arranged at the insertion portion.

17 Claims, 7 Drawing Sheets

(51) Int. Cl.
*A61B 5/00* (2006.01)
*A61B 17/00* (2006.01)
*A61B 34/00* (2016.01)
*A61B 34/20* (2016.01)
*A61B 5/09* (2006.01)
*A61B 1/00* (2006.01)
*A61B 90/30* (2016.01)
*A61B 90/00* (2016.01)

(52) U.S. Cl.
CPC .............. *A61B 5/09* (2013.01); *A61B 17/00* (2013.01); *A61B 34/20* (2016.02); *A61B 34/25* (2016.02); *A61B 2034/252* (2016.02); *A61B 2090/0807* (2016.02); *A61B 2090/309* (2016.02)

(56) References Cited

U.S. PATENT DOCUMENTS

| | | | | |
|---|---|---|---|---|
| 4,953,539 | A * | 9/1990 | Nakamura et al. | 600/109 |
| 5,273,025 | A * | 12/1993 | Sakiyama | A61B 1/05 |
| | | | | 128/899 |
| 5,295,483 | A * | 3/1994 | Nowacki et al. | 600/439 |
| 5,513,637 | A * | 5/1996 | Twiss | A61B 5/06 |
| | | | | 128/903 |
| 5,617,857 | A * | 4/1997 | Chader | A61B 5/06 |
| | | | | 128/899 |
| 5,682,890 | A * | 11/1997 | Kormos et al. | 600/417 |
| 6,063,022 | A * | 5/2000 | Ben-Haim | 600/41 |
| 6,468,204 | B2 * | 10/2002 | Sendai et al. | 600/160 |
| 6,675,040 | B1 * | 1/2004 | Cosman | 600/427 |
| 7,024,237 | B1 * | 4/2006 | Bova et al. | 600/429 |
| 7,871,370 | B2 * | 1/2011 | Sugimoto | 600/117 |
| 7,996,068 | B2 * | 8/2011 | Telischak | A61B 5/0071 |
| | | | | 600/431 |
| 8,031,227 | B2 * | 10/2011 | Neal et al. | 348/169 |
| 8,221,308 | B2 * | 7/2012 | Noguchi et al. | 600/117 |
| 8,500,771 | B2 * | 8/2013 | Isham | 606/197 |
| 8,679,147 | B2 * | 3/2014 | Isham | 606/197 |
| 8,845,524 | B2 * | 9/2014 | Belson et al. | 600/152 |
| 8,882,657 | B2 * | 11/2014 | Ohline | A61B 1/005 |
| | | | | 600/117 |
| 2002/0013512 | A1 * | 1/2002 | Sendai | A61B 5/0071 |
| | | | | 600/160 |
| 2004/0176683 | A1 * | 9/2004 | Whitin | A61B 5/06 |
| | | | | 600/424 |
| 2005/0070790 | A1 * | 3/2005 | Niwa et al. | 600/424 |
| 2006/0009679 | A1 * | 1/2006 | Ito | A61B 1/0005 |
| | | | | 600/117 |
| 2006/0056855 | A1 * | 3/2006 | Nakagawa | G09F 9/33 |
| | | | | 398/183 |
| 2007/0015966 | A1 * | 1/2007 | Niwa et al. | 600/115 |
| 2007/0043260 | A1 * | 2/2007 | Niwa et al. | 600/117 |
| 2007/0106114 | A1 * | 5/2007 | Sugimoto | A61B 1/31 |
| | | | | 600/117 |
| 2007/0238985 | A1 * | 10/2007 | Smith | A61B 5/06 |
| | | | | 600/424 |
| 2007/0249901 | A1 * | 10/2007 | Ohline | A61B 1/005 |
| | | | | 600/117 |
| 2008/0004529 | A1 * | 1/2008 | Kawashima et al. | 600/443 |
| 2008/0108901 | A1 * | 5/2008 | Baba | A61B 8/0833 |
| | | | | 600/459 |
| 2008/0116093 | A1 * | 5/2008 | Felten et al. | 206/316.2 |
| 2008/0146875 | A1 * | 6/2008 | Noguchi et al. | 600/117 |
| 2008/0269596 | A1 * | 10/2008 | Revie et al. | 600/424 |
| 2009/0054767 | A1 * | 2/2009 | Telischak | A61B 5/0071 |
| | | | | 600/431 |
| 2011/0130750 | A1 * | 6/2011 | Ormsby | A61B 18/1815 |
| | | | | 606/33 |
| 2012/0046536 | A1 * | 2/2012 | Cheung | A61C 1/082 |
| | | | | 600/407 |
| 2012/0316486 | A1 * | 12/2012 | Cheung | A61C 1/082 |
| | | | | 602/48 |
| 2012/0327205 | A1 * | 12/2012 | Takahashi | A61B 1/04 |
| | | | | 348/65 |
| 2013/0201320 | A1 * | 8/2013 | Watanabe | A61B 1/0638 |
| | | | | 348/77 |
| 2013/0261439 | A1 * | 10/2013 | Schmitt | A61B 6/032 |
| | | | | 600/424 |
| 2013/0276557 | A1 * | 10/2013 | Duindam | G01B 21/22 |
| | | | | 73/865.8 |

FOREIGN PATENT DOCUMENTS

| | | |
|---|---|---|
| JP | 4316118 | 8/2009 |
| JP | 2009-268617 A | 11/2009 |
| JP | WO 2010110138 A1 * | 9/2010 ........... A61B 1/0638 |

* cited by examiner

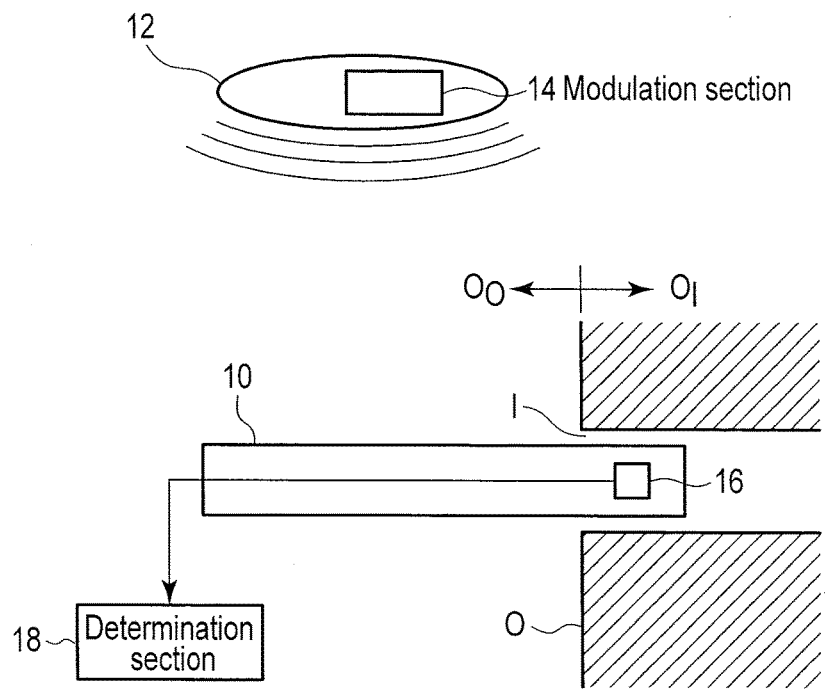
F I G. 1
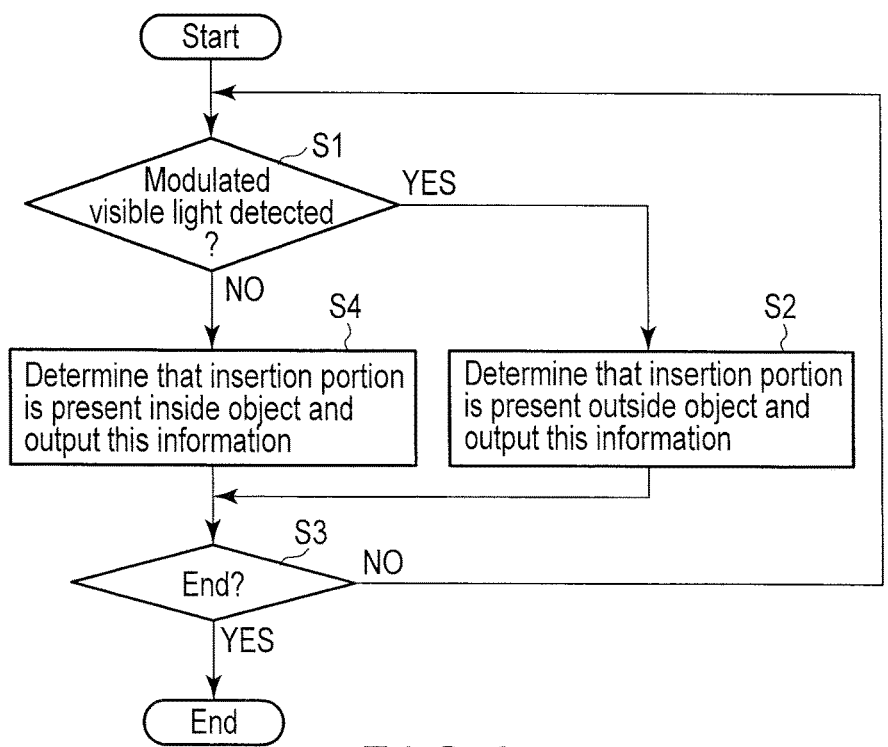
F I G. 2

ENDOSCOPE DETECTING SYSTEM

CROSS REFERENCE TO RELATED APPLICATIONS

This application is a Continuation application of PCT Application No. PCT/JP2012/050829, filed Jan. 17, 2012 and based upon and claiming the benefit of priority from prior Japanese Patent Application No. 2011-011871, filed Jan. 24, 2011, the entire contents of all of which are incorporated herein by reference.

BACKGROUND OF THE INVENTION

1. Field of the Invention

The present invention relates to an endoscope system which an insertion portion of an endoscope is inserted from an insertion opening of an object to observe an inner surface of the object.

2. Description of the Related Art

In an endoscope, as a light source configured to illuminate an inner surface of an object which is an observation target, a light source having a small luminous point such as a laser or a light source that radiates light having relatively high energy like ultraviolet light or blue light is used.

With respect to radiated light radiated from such a light source apparatus, a maximum permissible exposure (MPE) of a human body largely varies depending on eyes and skin. That is, the MPE for the eyes has a value which is several score times larger than the MPE for skin. Thus, in a medical endoscope, there has been desired detection means for detecting whether an insertion portion of an endoscope having an illumination light emitting portion arranged at a distal end thereof. When such detection means is provided, a light volume upper limit based the MPE for eyes is set for the outside of a body, a light volume upper limit for skin is set for the inside of a body, and control can be effected so that the light source can emit light with a light volume required for observation.

Further, for the purpose of preventing a subject from feeling annoyed with glare, detection means for detecting that an insertion portion is present inside or outside a body is desired.

On the other hand, in an industrial endoscope, to extend life duration of a light source apparatus or achieve power saving, when the insertion portion is present outside an observation target object, detection means for detecting the inside or the outside of the observation target object is likewise desired for the purpose of stopping or dimming the light source.

In contrast, Japanese Patent No. 4316118 discloses a technology that detects the inside of a living body or the outside of a living body by detecting flicker of a fluorescent lamp by means of a detector disposed at a distal end of a scope.

However, the technology disclosed in Japanese Patent No. 4316118 uses the flicker of the fluorescent lamp. Therefore, in the medical endoscope cannot detect that the insertion portion is present in the inside or the outside of a body in an examination room where the fluorescent lamp is not used. On the other hand, in the industrial endoscope, whether the insertion portion is present in the inside or the outside of the observation target object cannot be detected in an outdoor usage environment. Further, even in a case where a fluorescent lamp is provided in a room, if any other illumination apparatus is also provided, flicker of the fluorescent lamp is masked by light from the apparatus and may not be detected with certainty.

In view of the above-described problems, it is an object of the present invention to provide an endoscope system that can detect with certainty that an insertion portion of an endoscope is present inside or outside an object.

BRIEF SUMMARY OF THE INVENTION

According to an aspect of the invention, there is provided an endoscope system which an insertion portion of an endoscope is inserted from an insertion opening of an object to observe an inner surface of the object, comprising:

an illumination unit which includes a modulation section configured to control a visible light source so that visible light from the visible light source is subjected to intensity modulation in a predetermined pattern, and emits modulated visible light as illumination light;

a detection section configured to detect the modulated visible light; and a determination section configured to determine whether the insertion portion is present in the object based on a detection result of the detection section, wherein the illumination unit is arranged outside the object, and the detection section is arranged at the insertion portion.

According to the present invention, it is possible to provide an endoscope system that allows the illumination unit to actively emit visible light having intensity modulated in a predetermined pattern, determines whether an insertion portion of an endoscope is present in an object based on a detection state of the modulated visible light at the insertion portion of the endoscope, and hence can detect with certainty that the insertion portion of the endoscope is present inside or outside the object.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic block diagram of an endoscope system according to a first embodiment of the present invention;

FIG. 2 is a view showing an operation flowchart of a determination section in the endoscope system according to the first embodiment;

DETAILED DESCRIPTION OF THE INVENTION

Figure 3:
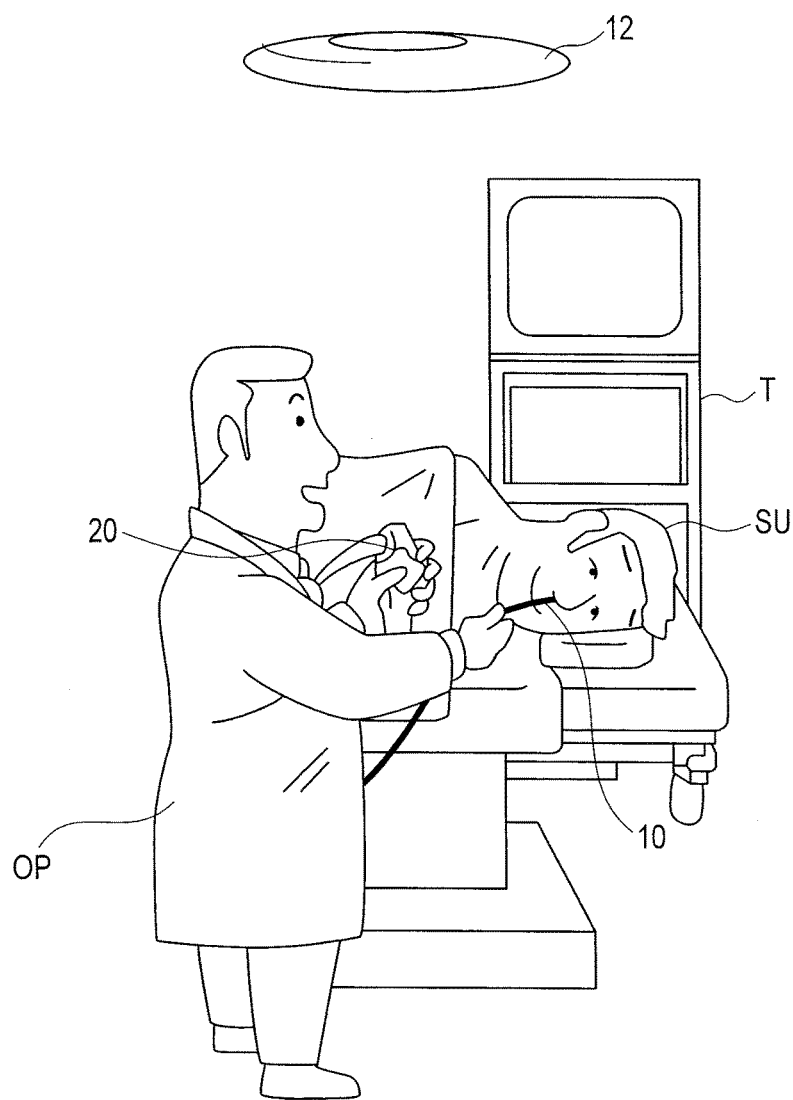
FIG. 3 is a view showing an example of an operating status of the endoscope system according to the first embodiment.

Embodiments of the present invention will now be described with reference to the drawings.

First Embodiment

As shown in FIG. 1, an endoscope system according to a first embodiment of the present invention includes an insertion portion 10, an illumination unit 12 including a modulation section 14, a detection section 16, and a determination section 18. The insertion portion 10 is an insertion portion of an endoscope, the insertion portion of the endoscope being inserted into an insertion opening I of an object O. The modulation section 14 controls a visible light source in such a manner that visible light from the visible light source can be subjected to intensity modulation (blinking) in a predetermined pattern. The illumination unit 12 emits the visible light subjected to the intensity modulation in the predetermined pattern (which will be referred to as modulated visible light hereinafter) by the modulation section 14 as illumination light. The detection section 16 detects the modulated visible light emitted from the illumination unit 12. The determination section 18 determines whether the insertion portion 10 is present in the inside of object $O_I$ based on a detection result from the detection section 16. Here, the illumination unit 12 is arranged in the outside of object $O_O$, and the detection section 16 is arranged at the insertion section 10.

In such an endoscope system, as shown in FIG. 2, the determination section 18 first receives a detection result from the detection section 16 with start of an operation of the endoscope, and determines whether the detection section 16 has detected the modulated visible light based on this detection result (step S1). Here, if the determination section 18 has determined that the detection section 16 detected the modulated visible light, it determines that the insertion portion 10 is present in the outside of object $O_O$, and outputs this information (step S2). Then, the determination section 18 determines whether the operation of the endoscope has been finished (step S3), and it returns to the operation in step S1 if the operation has not been finished.

On the other hand, if the insertion portion 10 is present in the inside of object $O_I$, the modulated visible light is blocked by the object O and does not enter the detection section 16. Therefore, if the determination section 18 has been determined that the detection portion 16 abandoned detecting the modulated visible light in step S1, the determination section 18 determines that the insertion portion 10 is present in the inside of object $O_I$ and outputs this information (step S4). Then, the determination section 18 advances to the operation of step S3, determines whether the operation of the endoscope has been terminated, and returns to the operation of step S1 if the operation has not been terminated.

Further, if the determination section 18 has determined that the operation of the endoscope has been terminated in step S3, it terminates the operation.

It is to be noted that any determination result is output here, but outputting at least one determination result enables a member that receives outputs from the determination section 18 to recognize in which one of the inside of object $O_I$ and the outside of object $O_O$ the insertion portion 10 is present based on whether the determination result is output.

A more specific configuration will now be described based on an example where the endoscope is a medical endoscope that inserts the insertion portion 10 into a lumen of a living body and uses it.

As shown in FIG. 3, at the time of endoscopic observation, an operator OP, for example, a physician holds an operating portion 20 of the endoscope with his/her left hand, holds the insertion portion 10 with his/her right hand, and inserts the insertion portion 10 into the insertion opening I of the lumen of a subject SU, for example, a mouth or a nose.

The illumination unit 12 is arranged outside the lumen of a subject SU at a position where the insertion opening I of the lumen, which is provided near the operator's hands, can be illuminated at the time of inserting the insertion portion 10 into the lumen. Specifically, the illumination unit 12 is disposed to, for example, a ceiling of an inspection room.

Figure 4:
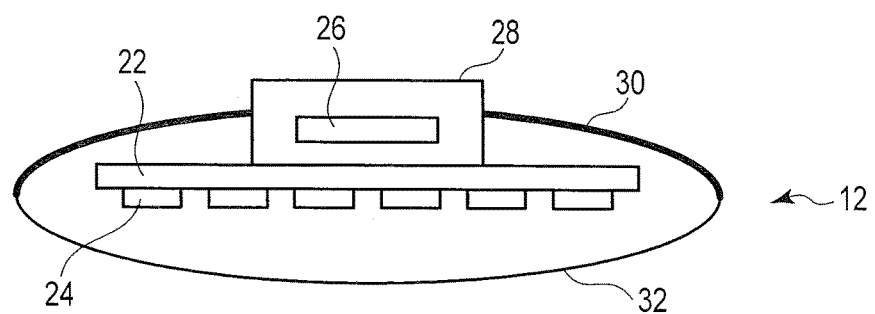
FIG. 4 is a cross-sectional view showing a configuration of an illumination unit in the endoscope system according to the first embodiment.

As shown in FIG. 4, the illumination unit 12 includes a substrate 22 having white LEDs 24 as illumination light sources mounted thereon and a control circuit 26 that controls light emission of the white LEDs 24. The control circuit 26 is configured to blink the white LEDs 24 and also has a function as the modulation section 14. It is to be noted that this predetermined pattern must be a pattern of blinking in a sufficiently fast cycle that humans cannot recognize the blinking and falsely recognizes that continuous lighting is carried out, for example, at a speed higher than 30 Hz, and particulars of this pattern will be described later.

Furthermore, the illumination unit 12 also includes a fixing portion 28 that is used for fixing the illumination unit 12 on a ceiling or the like, a housing 30 that surrounds the substrate 22, and an illumination light irradiation window 32 that applies illumination light (the modulated visible light) radiated from the white LEDs 24 to the outside.

Figure 5:
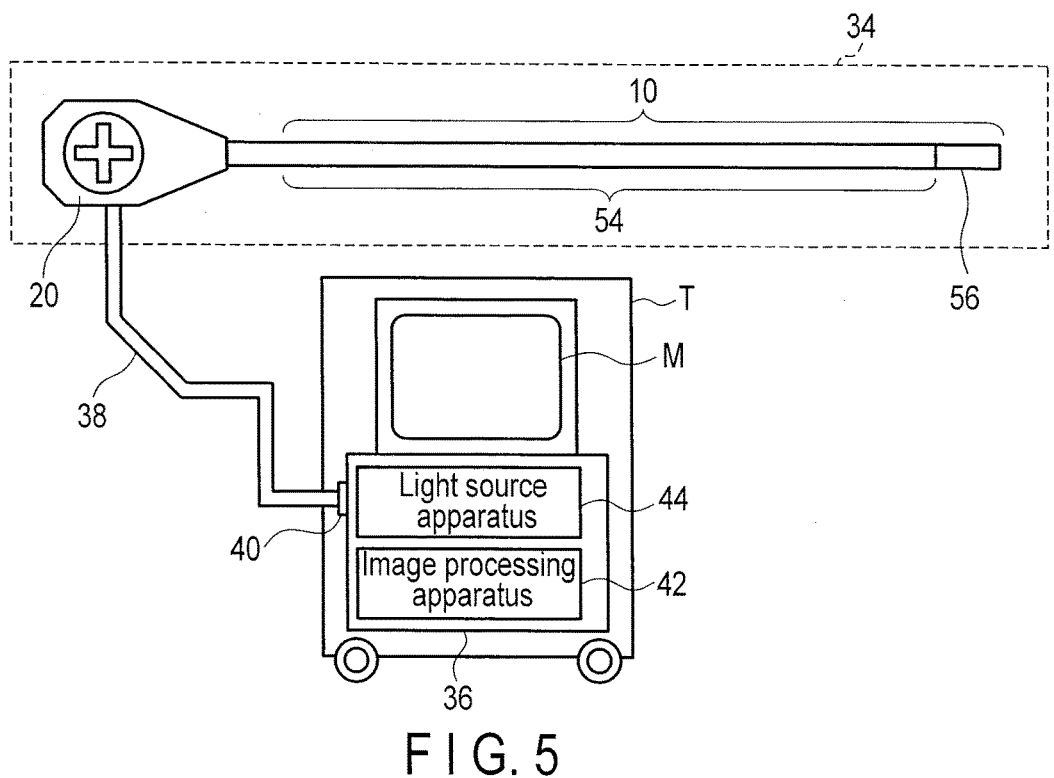
FIG. 5 is a view showing a configuration of an endoscope in the endoscope system according to the first embodiment.

On the other hand, as shown in FIG. 5, the medical endoscope can be divided into a scope section 34 which is held by an operator OP such as a physician to perform an operation and a main body section 36 mounted in a trolley T. Specifically, a connection cable 38 extending from the scope section 34 is attachable to or detachable from a connecting portion 40, for example, a connector or the like in the main body section 36.

It is to be noted that the trolley T means a movable rack in which the endoscope is mounted, and a monitor M, a printer that prints acquired images, and others as well as the main body section 36 are mounted. Although not shown in particular, a holding portion that holds the scope section 34 is provided in this trolley T so that the scope section 34 can be suspended and held in a state that the scope section 34 is connected to the main body section 36. At the time of use, the scope section 34 can be removed from the holding portion and then used.

The main body section 36 includes an image processing apparatus (a video processor) 42 and various other members required for endoscopic observation. The image processing apparatus 42 supplies electric power to the scope section 34 or processes images acquired by an imaging section (which will be described later) arranged at a distal end of the scope section 34. As other members, for example, a light source apparatus 44 configured to radiate illumination light from the distal end of the scope section 34 is included. The main body section 36 is connected to the monitor M which displays, for example, images acquired by the imaging section.

It is to be noted that the determination section 18 may be configured in the image processing apparatus 42, may be configured in the light source apparatus 44, or may be configured in the main body section 36 to be independent from these members.

Furthermore, it is to be noted that FIG. 5 shows an example where the image processing apparatus 42 and the light source apparatus 44 are incorporated in one housing of the main body section 36. However, the apparatuses may be combined by using different housings so that one main body section 36 can be configured.

Figure 6:
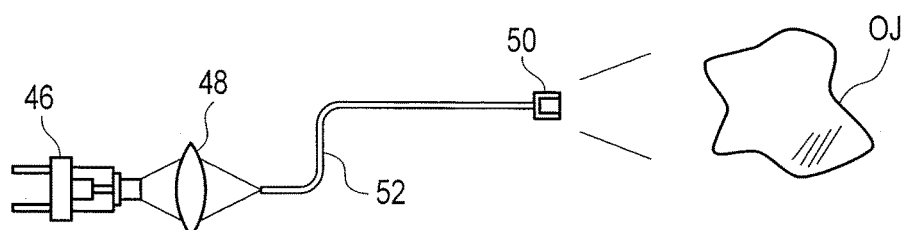
FIG. 6 is a view showing a configuration concerning illumination of the endoscope in FIG. 5.

For example, as shown in FIG. 6, the light source apparatus 44 includes an excitation light source 46, an optical system 48, and a light source control section (not shown). The excitation light source 46 is a laser with a small luminous point or an LED that emits light that has relatively high energy such as ultraviolet light or blue light. The optical system 48 condenses excitation light from the excitation light source 46. The light source control section controls an amount of luminescence or light emission timing of the excitation light source 46. On the other hand, an illumination object OJ must be illuminated with light having a wavelength suitable for observation, for example, white light. Thus, a wavelength converting section 50 is mounted at a distal end portion of the scope section 34. Furthermore, the excitation light source 46 and the wavelength converting section 50 are connected through an optical fiber 52. That is, the optical fiber 52 is arranged in the connection cable 38 and the scope section 34. Therefore, when the wavelength converting section 50 is irradiated with the excitation light emitted from the excitation light source 46 through the optical fiber 52, the wavelength converting section 50 radiates the illumination light, and the illumination light is applied to the illumination object OJ.

In addition, it is needless to say an electric wiring line as well as the optical fiber 52 is formed in the connection cable 38 between the scope section 34 and the main body section 36.

Figure 7:
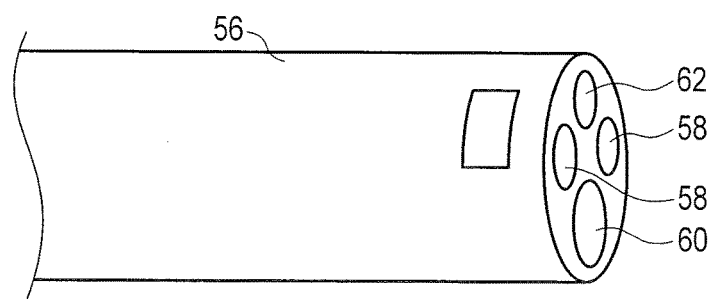
FIG. 7 is a perspective view showing a scope distal end portion of the endoscope in FIG. 5.

On the other hand, as described above, the scope section 34 is constituted of the insertion portion 10 which is held at a position near the distal end thereof with a right hand of the operator OP, for example, a physician and operated to be inserted into a lumen of a living body and the operating portion 20 which is held with a left hand of the operator and operated. The insertion portion 10 is constituted of a bending portion 54 and a hard portion 56. The bending portion 54 is configured to be readily bendable in accordance with bend of the lumen, and it bends in response to an operation of the operating portion 20 or an operation of the operator OP, for example, a physician. The hard portion 56 is provided at a distal end portion of the bending portion 54, and it does not deform. As shown in FIG. 7, on a distal end surface of this hard portion are provided two illumination light emitting portions 58 from which illumination light emits, an imaging section 60 which acquires images of an illumination object OJ irradiated with the illumination light, and a channel 62 into which a forceps or the like is inserted. The wavelength converting section 50 is mounted in the hard portion 56 for the illumination light emitting portions 58. Further, an imaging optical system and a non-illustrated imaging element such as a CCD that can detect visible light are mounted in the hard portion 56 for the imaging section 60.

Here, since the imaging element of the imaging section 60 can detect the visible light, it can detect modulated illumination light (white light) radiated from the white LEDs 24 in the illumination unit 12. Therefore, in this embodiment, the imaging element is used as the detection section 16 to detect the modulated illumination light.

It is to be noted that the imaging element acquires images at a predetermined frame rate, for example, 30 frames/second and transfers data to the determination section 18 configured in, for example, the image processing apparatus 42 in the main body section 36 through a non-illustrated signal wiring line extending in the insertion portion 10, the operating portion 20, and the connection cable 38.

At this time, if the predetermined pattern in the blinking of the white LEDs 24 in the illumination unit 12 is the same as the frame rate of the imaging element or an integral multiple of the same, the determination section 18 cannot distinguish the blinking from the continuous lighting. Thus, the control circuit 26 of the illumination unit 12 must blink the white LEDs 24 in a blinking pattern in a cycle different from the frame rate of the imaging element.

Figure 8:
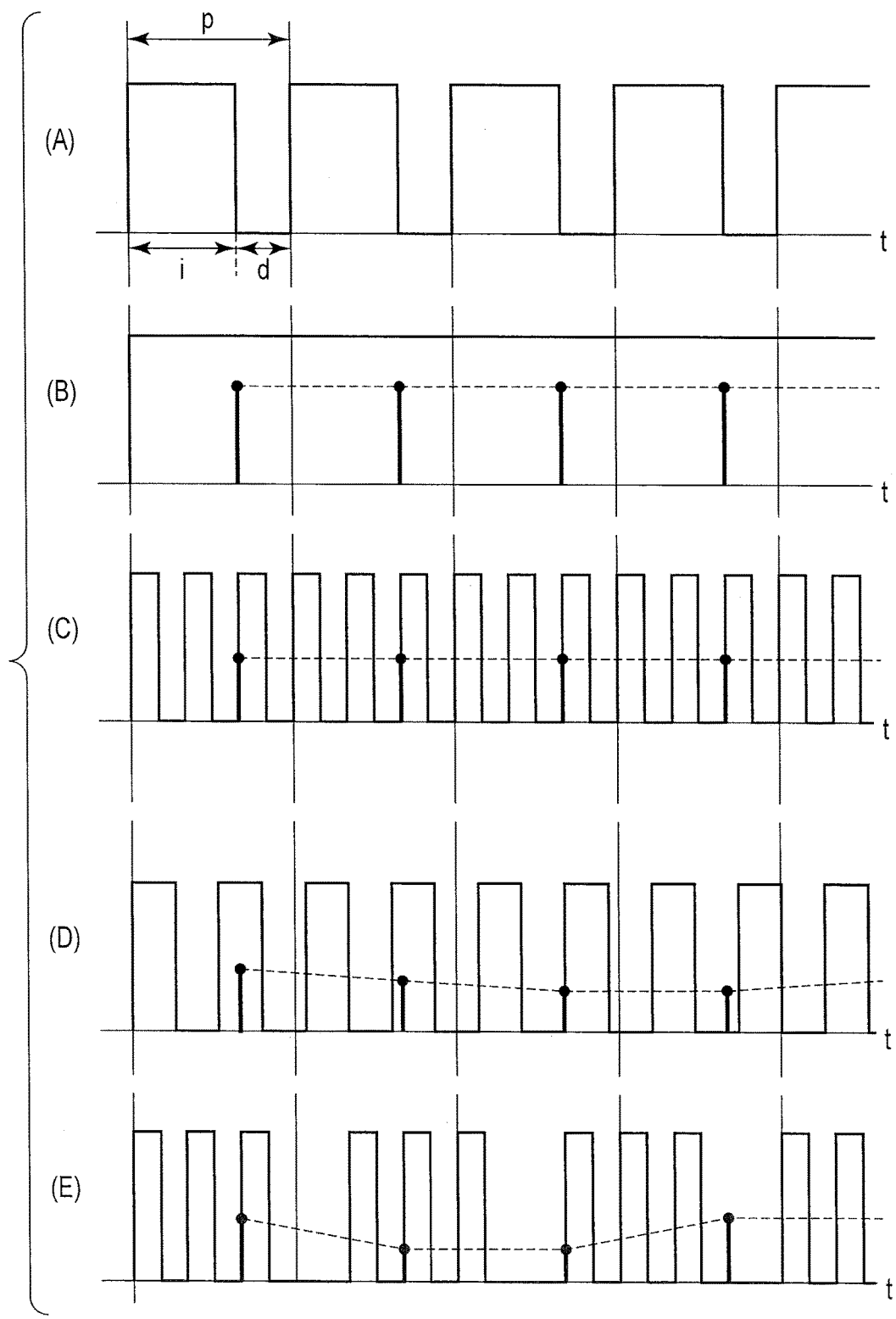
FIG. 8 is a view for explaining a function of a modulation section in the endoscope system according to the first embodiment.

That is, a timing chart (A) in FIG. 8 shows an example of the frame rate of the imaging element. One cycle p of the imaging element is constituted of an image acquisition period i during which each image is acquired and a data transfer period d during which acquired image data is transferred to a processing circuit in the image processing apparatus 42. This one cycle p is 1/30 second in case of the frame rate which is 30 frames/second.

In FIG. 8, a timing chart (B) shows an example that the white LEDs 24 of the illumination unit 12 are subjected to the continuous lighting.

It is to be noted that, in each of timing charts (B) to (E) in FIG. 8, a high level of a waveform indicated by a solid line represents lighting and a low level of the same represents extinction, respectively. Moreover, each thick vertical line with a dark circle represents an amount of detection signals acquired during the image acquisition period i that is finished at a position of this line, and a length (a height) is a rough standard for a signal amount. It is to be noted that each of the timing charts 8(B) to (E) shows an amount of detection signals when the same subject, for example, a white plate was imaged for comparison.

As shown in the timing chart (B), in the state of the continuous lighting, the detection signals from the imaging element are uniform. On the other hand, the timing chat (C) shows an example when the white LEDs 24 of the illumination unit 12 are blinked in a cycle that is just triple the frame rate. During the image acquisition period i of the imaging element, the illumination light is constantly emitted twice. Since a light volume detected by the imaging element is time integration of the light emission effected twice, the detected light volume does not vary. As a result, since the uniform detection signals alone are obtained like the constant lighting, the determination section 18 cannot detect the blinking of the illumination unit 12, i.e., presence/absence of the modulated visible light.

In the timing chart (D), a cycle (which is a cycle that is 15/8-fold of the frame rate and not an integral multiple) different from that described above is adopted, a light volume detected by the imaging element varies with time. As a result, the determination section 18 can detect the blinking of the illumination unit 12, i.e., presence/absence of the modulated visible light.

Additionally, in the timing chart 8(E), although each blinking is triple the frame rate that is the same as that in the timing chart (C), the blinking has a pattern that the lighting is performed three times and then a pause is interposed. That is, a cycle is ¾-fold of the frame rate, and it is not an integral multiple of the frame rate either. Therefore, the determination section 18 can detect the blinking of the illumination unit 12, i.e., presence/absence of the modulated visible light.

Although the plain explanation has been given in the example of FIG. 8, when the blinking is actually effected in a more complicated pattern at a higher speed than the frame rate, the modulated visible light can be detected easily and with certainty.

As described above, the endoscope system using the medical endoscope is configured in such a manner that the modulated visible light emitted from the illumination unit 12 is detected by using the imaging element of the imaging section 60 provided in the insertion portion 10 of the scope section 34 as the detection section 16. Further, at the time of inserting the insertion portion 10 into a lumen of the subject SU, the illumination unit 12 is previously installed at a position where the insertion opening I of the lumen provided near the hands of the operator OP can be illuminated. As a result, the modulated visible light can be applied with certainty to the insertion opening I of the lumen. Therefore, it is possible to substantially eliminate a possibility that the distal end of the scope section 34 is hidden behind the operator OP or any other interior member, the detection section 16 cannot detect the modulated visible light even though the distal end of the scope section 34 is present outside a body, and the determination section 18 determines that the distal end is present in the body. Furthermore, in this embodiment, the modulated visible light subjected to the intensity modulation in the predetermined pattern is actively emitted, and the inside of the body or the outside of the body can be detected with certainty without false detection based on whether the modulated visible light that coincides with the predetermined pattern has been detected. Moreover, in this embodiment, since the imaging element of the scope section 34 can be used as the detection section 16, a dedicated apparatus does not have to be disposed to the scope section 34, and it is possible to easily detect in which one of the inside of the lumen or the outside of the lumen the distal end of the scope section 34 is present.

It is to be noted that the determination section 18 is connected with a non-illustrated light source control section of the light source apparatus 44 and can output a determination result to the light source control section. As a result, the light source control section can set a light volume upper limit based on MPE for eyes in case of the outside of the body, assume a light volume upper limit based on MPE for skin in case of the inside of the body, and control the excitation light source 46 so that a light volume required for observation can be obtained.

Additionally, for example, the image processing apparatus 42 in the main body section 36 of the endoscope may have a function as a confirming section that confirms whether intensity modulation (blinking) of the modulated visible light of the illumination 12 can be detected when the insertion portion 10 is securely present outside the lumen immediately after turning on a power supply of the endoscope. When the operator OP is informed of a confirmation result of this confirming section, it is possible to eliminate a possibility that the operator OP may use the endoscope which does not normally operate. Further, the control circuit 26 that functions as the modulation section 14 of the illumination unit 12 may be configured to enable selectively switching a cycle of the intensity modulation of the illumination light, and it may perform changeover adjustment (calibration) to provide a detectable cycle by a wired or wireless switching operation of the operator OP. It is needless to say that the calibration may be automatically performed in accordance with a confirmation result from the confirming section without troubling the operator OP.

[Modification]

It is to be noted that, in this embodiment, when the imaging element also functions as the detection section 16, the example that the modulated illumination light (the white light) is also detected during the image detection period for detection of endoscopic images has been described. However, these two types of detection may be temporally separated from each other. That is, an image acquisition mode that the same imaging element is used to detect endoscopic images and detection mode that the modulated variable light is detected may be continuously repeated.

Figure 9:
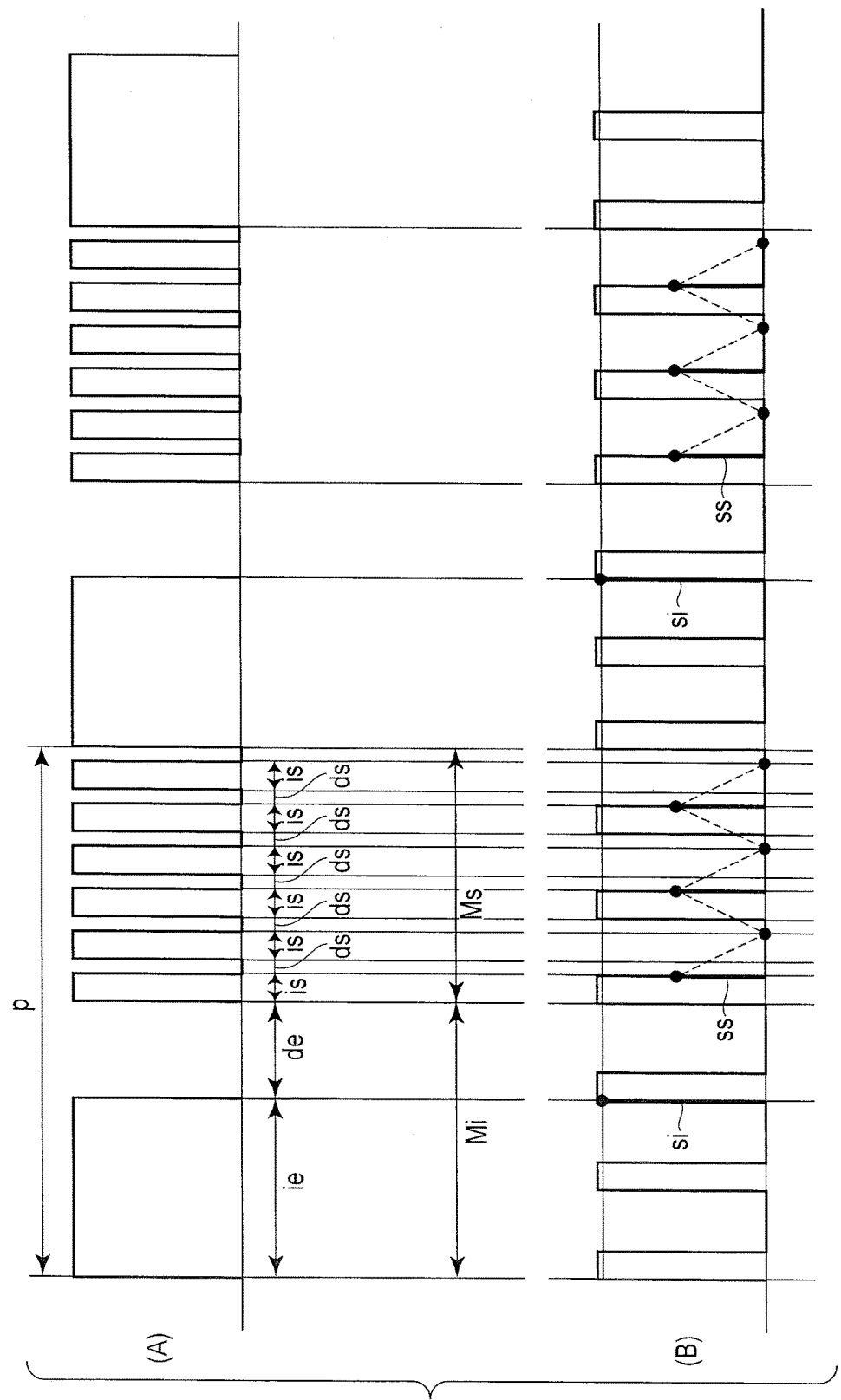
FIG. 9 is a view for explaining a function of a modulation section in an endoscope system according to a modification of the first embodiment.

A timing chart (A) in FIG. 9 shows such an example that one period p of the imaging system has a detection mode Ms in addition to an image acquisition mode Mi. The image acquisition mode Mi is constituted of an endoscopic image acquisition period ie and an endoscopic image data transfer period de. In the detection mode Ms, modulated variable light detection periods is and a detection data transfer period ds are repeated in a predetermined cycle. A timing chart (B) in FIG. 9 shows a modulation pattern (a blinking pattern) of the modulated illumination light (the white light) at this time and light signal amounts si and ss detected in the image acquisition mode Mi and the detection mode Ms.

In this example, a modulation cycle of the modulated visible light is set to an integral multiple of a cycle of the endoscopic image acquisition mode Mi. Furthermore, a detection cycle for detecting the modulated visible light in the detection mode Ms is set to an integral multiple of the modulation cycle of the modulated visible light. For example, the modulation cycle of the modulated visible light is set to a triple of the cycle of the image acquisition mode Mi, and the predetermined cycle for detecting the modulated visible light in the detection mode Ms is set to a double of the modulation cycle of the modulated visible light.

When this configuration is adopted, each light signal detected by the imaging element in the image acquisition mode Mi does not vary, and a change in modulated visible light can be detected with certainty. As a result, whether the insertion portion 10 is present inside or outside a body cavity can be securely detected, and an image which is free from flicker in a screen can be obtained even if the insertion portion 10 is present outside the body cavity.

Second Embodiment

A second embodiment according to the present invention will now be described.

It is to be noted that this second embodiment will be also explained as an endoscope system using a medical endoscope. A portion different from the first embodiment alone will be described below.

In the first embodiment, the imaging element of the imaging section 60 also functions as the detection section 16. On the other hand, in this second embodiment, modulated visible light (white light) emitted from an illumination unit 12 is detected by a dedicated illumination light detector instead of an imaging element.

Figure 10:
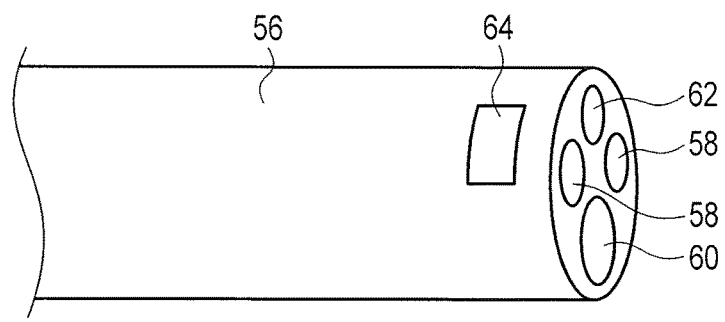
FIG. 10 is a view showing a configuration of a scope distal end portion of an endoscope in an endoscope system according to a second embodiment of the present invention.

That is, as shown in FIG. 10, a visible light detection section 64 as the detection section 16 is provided on a side surface of a hard portion 56 of an insertion portion 10. The visible light detection section 64 continuously receives the modulated visible light and discharges a current associated with an amount of received light. The discharged current is transmitted to a determination section 18 configured in, for example, an image processing apparatus 42 of a main body section 36 through a non-illustrated wiring line arranged in the insertion portion 10, an operating portion 20, and a connection cable 38.

It is to be noted that, when an IV conversion element is provide in the hard portion 56 and the current is converted into a voltage at a distal end portion of the insertion portion 10 to be transmitted to the determination section 18 as a voltage signal, a configuration that is hardly affected by noise and others can be realized.

Moreover, in regard to an installing position of the visible light detection section 64, it is possible to use a periaxial position of the hard portion 56 as long as it is a position at which the modulated visible light from the illumination unit 12 can be received when an operator OP holds the insertion portion 10 to insert into a lumen of a subject SU. However, it is more preferable to arrange the visible light detection section 64 in the hard portion 56 at a position where it faces the illumination unit 12, for example, the upper side when the illumination unit 12 is arranged on a ceiling side. As a result, stability of light reception of the modulated illumination light can be improved.

Additionally, in regard to a position along the longitudinal direction of the hard portion 56, there is an appropriate installing position which desirably enables determining that the insertion portion 10 is present in the inside of object $O_I$, i.e., the inside of a body when it is inserted to a given depth from an insertion opening I at the time of inserting the insertion portion 10 into a lumen of the subject SU. For example, in case of inserting the insertion portion 10 from the mouth which is a lumen into the stomach through the esophagus, a throat region of the subject SU must be brightly illuminated in order to securely perform the insertion into the esophagus. Therefore, considering a length from the lip region to the throat region which is a length in the mouth, it is specifically desirable to install the visible light detection section 64 in the range of approximately 5 cm from an end portion of the distal end of the hard portion 56. Further, to avoid detecting that the hard portion 56 is present in a body at the moment of inserting the hard portion 56 into the mouth, it is desirable to arrange the visible light detection section 64 at a position within 1 cm or more from the end portion.

In the endoscope system according to this embodiment, since the modulated visible light (the white light) emitted from the illumination unit 12 is detected by the dedicated visible light detection section 64, the modulation cycle can be set without considering the frame rate of the imaging element. Therefore, the modulation cycle which is an integral multiple of the frame rate of the imaging element can be set, and images of the imaging element are not affected. That is, each image is acquired in a constantly stable light emission state, and shading of the screen is not changed under the influence of the modulated visible light.

As described above, in this embodiment, providing the dedicated visible light detection section 64 as the detection section 16 can realize the more stable and assured detection. Furthermore, the modulation cycle that does not affect images of the imaging element can be selected.

It is to be noted that a degree of insertion of the hard portion 56 at the distal end of the insertion portion 10 into a lumen may be detected by providing the visible light detection sections 64 along the longitudinal direction of the hard portion 56 and taking a difference between detection intensities of these sections.

Third Embodiment

A third embodiment according to the present invention will now be described.

It is to be noted that this third embodiment will be also explained as an endoscope system using a medical endoscope. A portion different from the first and second embodiments alone will be described hereinafter.

According to this embodiment, an additional function is provided to the first or second embodiment concerning timing of an illumination unit 12 for modulating visible light. That is, in this embodiment, modulated visible light is emitted in accordance with an operating state of an endoscope.

Figure 11:
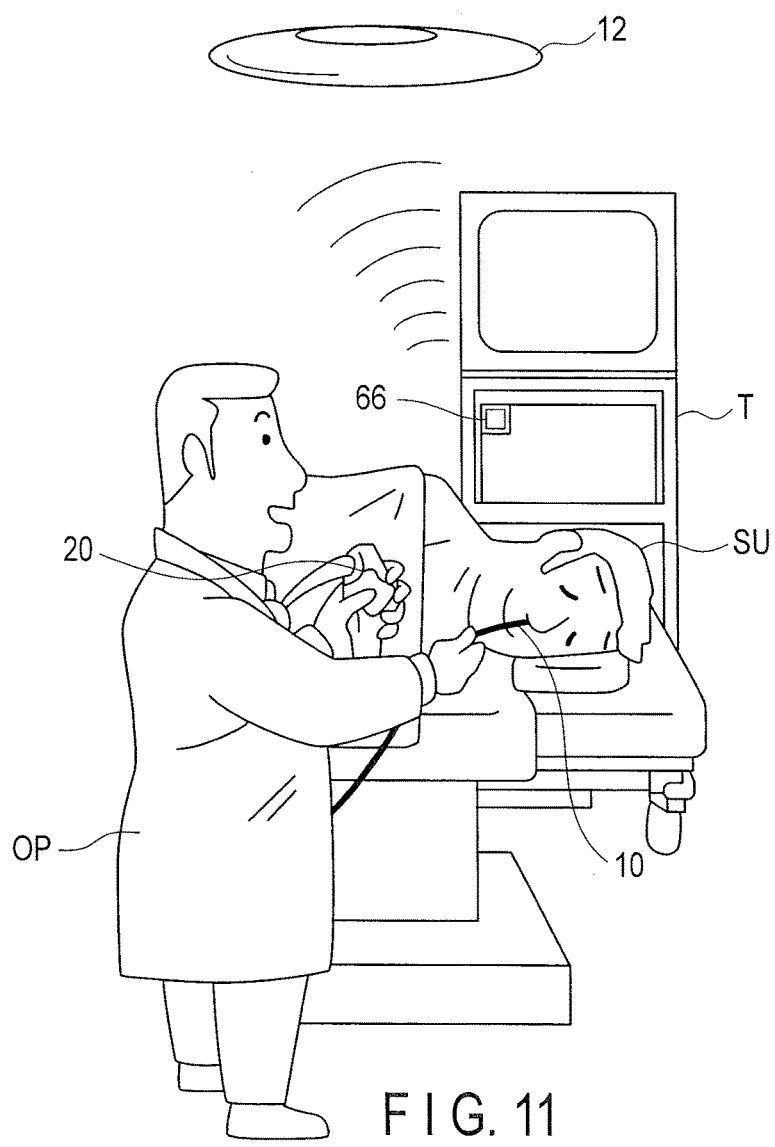
FIG. 11 is a view showing an example of an operating status of an endoscope system according to a third embodiment of the present invention.

Specifically, as shown in FIG. 11, a electromagnetic wave transmitter 66 is provided on part of a main body section 36 of the endoscope. In a state that a power supply of the main body section 36 of the endoscope is turned on and observation is possible, this electromagnetic wave transmitter 66 transmits electromagnetic waves toward the illumination unit 12.

Figure 12:
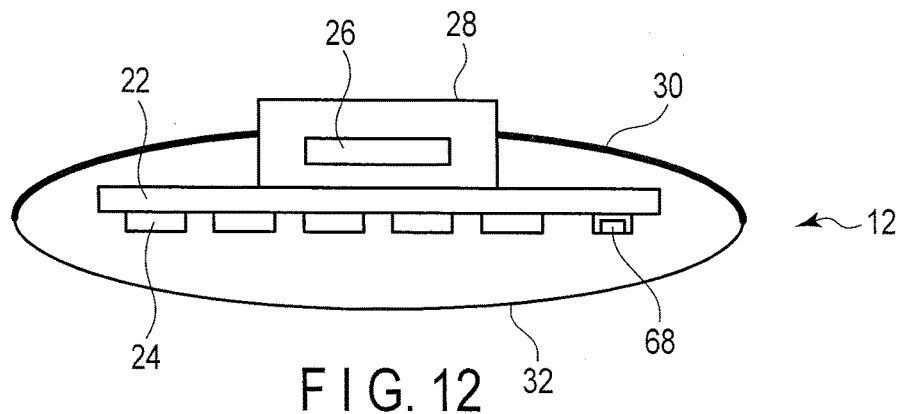
FIG. 12 is a view showing a configuration of an illumination unit in the endoscope system according to the third embodiment.

On the other hand, as shown in FIG. 12, in the illumination unit 12, an electromagnetic wave receiver 68 is provided on a substrate 22.

Figure 13:
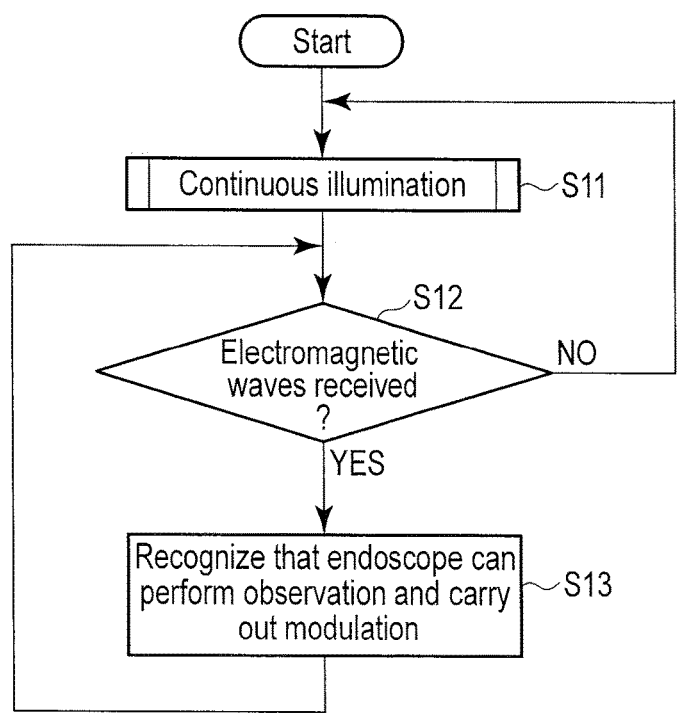
FIG. 13 is a view showing an operation flowchart of a control circuit of an illumination unit in FIG. 12.

In such a configuration, as shown in FIG. 13, a control circuit 26 of the illumination unit 12 starts an operation when a non-illustrated illumination switch is turned on, and it first performs a regular illuminating operation (step S11). It is to be noted that, in this regular illuminating operation, the white LEDs 24 can be continuously lighted to improve brightness, or a light volume, a modulation pattern, or the like can be freely set by using, for example, a desired power saving mode irrespective of the endoscope.

Then, a control circuit 26 determines whether the electromagnetic wave receiver 68 is receiving electromagnetic waves transmitted from the electromagnetic wave transmitter 66 in the endoscope, thereby recognizing whether the endoscope can perform observation (step S12). Here, when it has been determined that the electromagnetic wave receiver 68 has not been receiving the electromagnetic waves, the control circuit 26 determines that the endoscope cannot perform the observation, returns to the operation of step S11, and continues the regular illuminating operation.

On the other hand, when it has been determined that the electromagnetic wave receiver 68 has been receiving the electromagnetic waves, the control circuit 26 recognizes that the endoscope can perform the observation and controls the white LEDs 24 so that the visible light can be modulated in a predetermined modulation pattern (step S13). Thereafter, the control circuit 26 returns to the operation of step S12 and keeps emitting the modulated visible light while the electromagnetic wave receiver 68 is receiving the electromagnetic waves, i.e., while electric power is being supplied to the endoscope.

Moreover, when the electric power supplied to the endoscope is interrupted and the electromagnetic wave transmitter 66 terminates transmission of the electromagnetic waves, the control circuit 26 determines that the electromagnetic wave receiver 68 is not receiving the electromagnetic waves in step S12 and returns to the regular illuminating operation of step S11.

As described above, in this embodiment, the illumination unit 12 recognizes that the electric power is supplied to the endoscope to enable the observation, and it starts modulation of the visible light in the predetermined modulation pattern. Therefore, since a modulation section 14 operates in tandem with an operating status of the endoscope, the illumination unit 12 can emit light with various kinds of intensities, modulation patterns, and others, for example, continuous lighting irrespective of the endoscope in a state that the electric power is not supplied to the endoscope.

It is to be noted that wireless communication using the electromagnetic waves is adopted here, but the present invention is not restricted thereto, and wireless communication using infrared rays or visible light may be utilized. Additionally, cable communication may be used in place of wireless communication, and the communication can be effected with greater certainty in this case.

Further, presence or absence of the electromagnetic waves is not only determined, but any information may be transmitted from the main body section 36 of the endoscope to the control circuit 26 of the illumination unit 12 through the electromagnetic waves so that the control circuit 26 can operate based on this information. For example, modulation cycle switching information based on a confirmation result of a confirming section, which confirms if intensity modulation (blinking) of the modulated visible light by the illumination unit 12 can be detected, in the calibration described in the first embodiment can be transmitted from the main body section 36 to the control circuit 26, thereby executing the calibration.

Although the present invention has been described based on the embodiments, the present invention is not restricted to the foregoing embodiments, and it can be modified or applied in many ways within the gist of the present invention as a matter of course.

For example, in each of the first to third embodiments, the example of the medical endoscope has been described, but the present invention can be likewise applied to an industrial endoscope. In this case, the determination section 18 can be connected to a non-illustrated light source control section of a light source apparatus 44, and it can output its determination result to the light source control section. As a result, the light source control section can dim or stop illumination light in order to extend life duration of the light source apparatus 44 or achieve power saving in case of the outside of object $O_O$, or it can control an excitation light source 46 so that a light volume required for observation can be obtained in case of the inside of object $O_I$.

Additionally, the light source apparatus 44 may use a scattering section that performs scattering without converting a wavelength, or an emitting light characteristic converting section that converts a spread angle of a beam, in place of the wavelength converting section 50.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An endoscope system comprising:
   an endoscope having an insertion portion inserted into an insertion opening of an object to observe an inner surface of the object, the insertion portion having a detector arranged at an external surface of the insertion portion;
   an illumination unit including:
   a visible light source configured to direct visible light towards the detector; and
   a modulator configured to control the visible light source so that the visible light from the visible light source has a predetermined intensity modulation pattern, the predetermined intensity modulation pattern having a predetermined intensity pattern that varies with time;
   wherein the visible light source being configured to at least emit modulated visible light having the predetermined intensity modulation pattern from the visible light source as illumination light and the detector being configured to detect the modulated visible light; and
   a processor comprising hardware, the processor having a determination section configured to determine whether at least a portion of the insertion portion is present in the object based on a detection criteria, the detection criteria being whether or not the detector detects the predetermined intensity modulation pattern of the visible light;
   wherein
   the endoscope has an imaging element configured to acquire an endoscopic image,
   the detector also functions as the imaging element, and
   the imaging element has an image acquisition mode in which the endoscopic image is acquired and a detection mode in which the modulated visible light is detected.

2. The system according to claim 1, wherein the inner surface of the object is a lumen of a living body,
   the illumination unit is arranged outside the lumen, and
   the detector is arranged at the insertion portion.

3. The system according to claim 2, wherein the illumination unit is arranged at a position where illuminating an insertion opening of the lumen is enabled at the time of inserting the insertion portion into the lumen of the living body.

4. The system according to claim 1, wherein the modulator operates in tandem with an operating status of the endoscope.

5. The system according to claim 1, wherein the visible light source of the illumination unit is a light source configured to radiate white light and to use a white LED being able to modulate intensity of light.

6. The system according to claim 5, wherein the modulator operates in tandem with an operating status of the endoscope.

7. The system according to claim 1, wherein
   the endoscope is dividable into a scope section having the insertion portion and a main body section configured to process and display an observation image observed through the scope section,
   the determination section is configured in the main body section, and
   the detector is incorporated in a distal end portion of the insertion portion.

8. The system according to claim 7, wherein the modulator operates in tandem with an operating status of the endoscope.

9. The system according to claim 7, wherein the detector is arranged at the distal end portion of the insertion portion at a position where it faces the illumination unit at the time of inserting the insertion portion into the lumen of the living body.

10. The system according to claim 9, wherein the modulator operates in tandem with an operating status of the endoscope.

11. The system according to claim 1, wherein
the modulator controls the visible light source in such a manner that a cycle of the intensity pattern of the visible light varies with time to have a cycle different from an integral multiple of a frame rate of the imaging element.

12. The system according to claim 11, wherein the modulator operates in tandem with an operating status of the endoscope.

13. The system according to claim 1, wherein the modulator operates in tandem with an operating status of the endoscope.

14. The system according to claim 1, further comprising a confirming section configured to confirm whether detection of the modulated visible light by the detector is possible.

15. The system according to claim 14, wherein the modulator operates in tandem with an operating status of the endoscope.

16. The system according to claim 1, wherein the predetermined intensity modulation pattern is a blinking pattern.

17. The system according to claim 1, further comprising:
a light source apparatus configured to irradiate illumination light to the inside of the object, the light source apparatus being switchable between a first mode outputting illumination light having a first light volume for the inside of the object and a second mode having a second light volume for outside of the object, the first light volume being greater than the second light volume,
wherein the determination section is further configured to switch the light source apparatus from the second mode to the first mode when it is determined that the insertion portion is present in the object.

* * * * *